(12) United States Patent  
Nakamura et al.

(10) Patent No.: US 8,529,591 B2  
(45) Date of Patent: Sep. 10, 2013

(54) ANASTOMOTIC INSTRUMENT, ENDOSCOPE SYSTEM, AND CONTROL METHOD OF ANASTOMOTIC INSTRUMENT

(75) Inventors: Takayuki Nakamura, Ashigarakami-gun (JP); Koji Yoshida, Ashigarakami-gun (JP); Nobuyuki Torisawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 230 days.

(21) Appl. No.: 13/083,194

(22) Filed: Apr. 8, 2011

(65) Prior Publication Data

US 2011/0257667 A1 Oct. 20, 2011

(30) Foreign Application Priority Data

Apr. 15, 2010 (JP) ................. 2010-093837

(51) Int. Cl.
*A61B 17/08* (2006.01)
*A61B 17/04* (2006.01)

(52) U.S. Cl.
USPC ........................................ 606/153; 227/175.1

(58) Field of Classification Search
USPC ................. 606/153, 213, 215, 216; 600/104; 227/175.1, 179.1, 180.1
See application file for complete search history.

(56) References Cited

U.S. PATENT DOCUMENTS

| | | | |
|---|---|---|---|
| 5,395,030 A | 3/1995 | Kuramoto et al. | |
| 6,126,058 A | 10/2000 | Adams et al. | |
| 7,141,055 B2 * | 11/2006 | Abrams et al. | 606/213 |
| 7,694,864 B2 * | 4/2010 | Okada et al. | 227/175.1 |
| 2006/0264707 A1 | 11/2006 | Kinney | |
| 2008/0154288 A1 | 6/2008 | Belson | |

FOREIGN PATENT DOCUMENTS

| | | |
|---|---|---|
| EP | 1 616 526 A1 | 1/2006 |
| JP | 4233656 B2 | 6/2000 |
| JP | 2004-065476 A | 3/2004 |
| JP | 2004-089442 A | 3/2004 |
| WO | 2007/050370 A2 | 5/2007 |

OTHER PUBLICATIONS

Communication, dated Aug. 4, 2011, issued in corresponding EP Application No. 11162151.2, 9 pages.

* cited by examiner

*Primary Examiner* — Julian Woo
(74) *Attorney, Agent, or Firm* — Sughrue Mion, PLLC

(57) ABSTRACT

An anastomotic instrument includes first and second units. The first unit is attached to a distal end portion of an insert section of an endoscope, and has a self-propellable apparatus and an anvil. The second unit is attached behind the first unit, and has a cartridge and a balloon. The insert section with the anastomotic instrument is inserted into the alimentary canal. In the alimentary canal, fluid is sucked out from space enclosed by the first and second unit through a suction port provided in the cartridge, to bring the space into negative pressure. While the alimentary canal is shrunk in the space, the second unit is shifted relative to the first unit. In a state where the shrunk alimentary canal is caught between the first and second units, a cutter resects living body tissue, and staples are struck to join edges of an incision of the alimentary canal.

9 Claims, 5 Drawing Sheets

ANASTOMOTIC INSTRUMENT, ENDOSCOPE SYSTEM, AND CONTROL METHOD OF ANASTOMOTIC INSTRUMENT

BACKGROUND OF THE INVENTION

1. Field of the Invention

The present invention relates to an anastomotic instrument that is inserted into the alimentary canal of a living body in conjunction with an insert section of an endoscope and anastomoses tissue of the alimentary canal, and an endoscope system having the anastomotic instrument, and a control method of the anastomotic instrument.

2. Description Related to the Prior Art

In a medical field, a surgical operation dealing with anastomosis by which the alimentary canal is partly removed and joined again is performed, in order to resect living body tissue of a tumor or the like that is borne in the interior wall of the alimentary canal such as the large and small intestine. An anastomotic instrument used in the anastomosis is composed of an insert section to be introduced into the alimentary canal, a handling section provided at a proximal end of the insert section, a cylindrical cutter provided at a distal end of the insert section to remove a tumor, and a stapler provided around the cutter to catch and join circumferential edges of the alimentary canal resected by the cutter by striking a staple (needle) therein (For example, Japanese Patent No. 4223656 and Japanese Patent Laid-Open Publication Nos. 2004-65476 and 2004-89442).

When anastomosis is performed on the alimentary canal with use of the above anastomotic instrument, an image capturing device such as an endoscope is prepared separately, and is inserted into the alimentary canal from a position different from that of the anastomotic instrument. Thus, the anastomosis is carried out, while a position of living body tissue to be resected is checked with the image capturing device. In another case, if living body tissue to be resected is situated near an entrance of the alimentary canal, a distance to the tissue may be measured in advance by the image capturing device, palpation, or the like, in order to adjust an insertion amount of the anastomotic instrument in accordance with the measured distance.

However, the alimentary canal includes organs into which only the anastomotic instrument can be inserted, but the image capturing device cannot be inserted from a position different from that of the anastomotic instrument. Furthermore, if living body tissue to be resected is in the depths of the alimentary canal far from its entrance, a distance to the tissue cannot be measured in advance. Therefore, the surgical operation using the conventional anastomotic instrument cannot be performed in those cases. The living body tissue requiring the anastomosis is situated in various positions, and it is desirable to allow resection of the living body tissue even in the depths of the alimentary canal.

SUMMARY OF THE INVENTION

An object of the present invention is to provide an anastomotic instrument that can surely resect living body tissue situated in the depths of the alimentary canal, an endoscope system having the anastomotic instrument, and a control method of the anastomotic instrument.

To achieve the above and other objects of the present invention, an anastomotic instrument according to the present invention includes a first unit, a second unit, a suction device, a resecting device, and a fastening device. The first unit is attached to an insert section of an endoscope to be inserted into the alimentary canal on the side of a distal end of the insert section. The second unit is set on the insert section on the side of a proximal end of the insert section relative to the first unit. The suction device sucks out fluid from space enclosed by the first and second units in the alimentary canal so as to bring the space into negative pressure, and shrinks the alimentary canal in the space. The resecting device shifts one of the first and second units relative to the other, and resects living body tissue of the alimentary canal in a state of being caught between the first and second units. The fastening device joins the alimentary canal so as to close an incision of the living body tissue.

The resecting device preferably includes a cylindrical cutter. The cutter protrudes from an opposed surface across which the first and second units are opposed, and cuts the living body tissue. The fastening device preferably includes a staple. The staple is struck around the cutter by a stapler to join edges of the incision of the alimentary canal resected by the cutter.

At least one of the first and second units preferably has a self-propellable apparatus for propelling the insert section into the depths of the alimentary canal. At least one of the first and second units preferably has a balloon to be expanded with air sent inside. While the suction device is reducing pressure of the space enclosed by the first and second units, the first and second units tightly seal the space by the self-propelling apparatus or the balloon making contact with the alimentary canal.

The anastomotic instrument may further include a pressure gage for detecting the pressure of the space enclosed by the first and second units, while the suction device is sucking out the fluid from the space.

A first sheath may be coupled to the first unit, and a second sheath may be coupled to the second unit. The first and second sheaths are preferably fitted on the insert section.

An endoscope system according to the present invention includes an endoscope and the anastomotic instrument described above. The endoscope includes the insert section to be introduced into the alimentary canal, and a handling section coupled to the insert section and used in operation of the endoscope.

A control method of the anastomotic instrument according to the present invention includes the steps of actuating the suction device to suck out the fluid from the space enclosed by the first and second units in the alimentary canal and reduce pressure of the space and shrink the alimentary canal in the space; shifting one of the first and second units relative to the other, such that the shrunk alimentary canal is caught between the first and second units; actuating the resecting device to resect the living body tissue of the alimentary canal in a state of being caught between the first and second units; and actuating the fastening device to join the alimentary canal after the resection of the living body tissue.

According to the present invention, after the fluid is sucked out from the space enclosed by the first and second units in the alimentary canal, and the space is brought into negative pressure, one of the first and second units is shifted relative to the other, such that the first and second units catch the alimentary canal in the space. The resecting device resects the living body tissue of the caught alimentary canal, and the fastening device joins the alimentary canal after the resection of the living body tissue. Therefore, it is possible to surely resect the living body tissue even in the depths of the alimentary canal.

BRIEF DESCRIPTION OF THE DRAWINGS

For more complete understanding of the present invention, and the advantage thereof, reference is now made to the following descriptions taken in conjunction with the accompanying drawings, in which.

DESCRIPTION OF THE PREFERRED EMBODIMENTS

Figure 1:
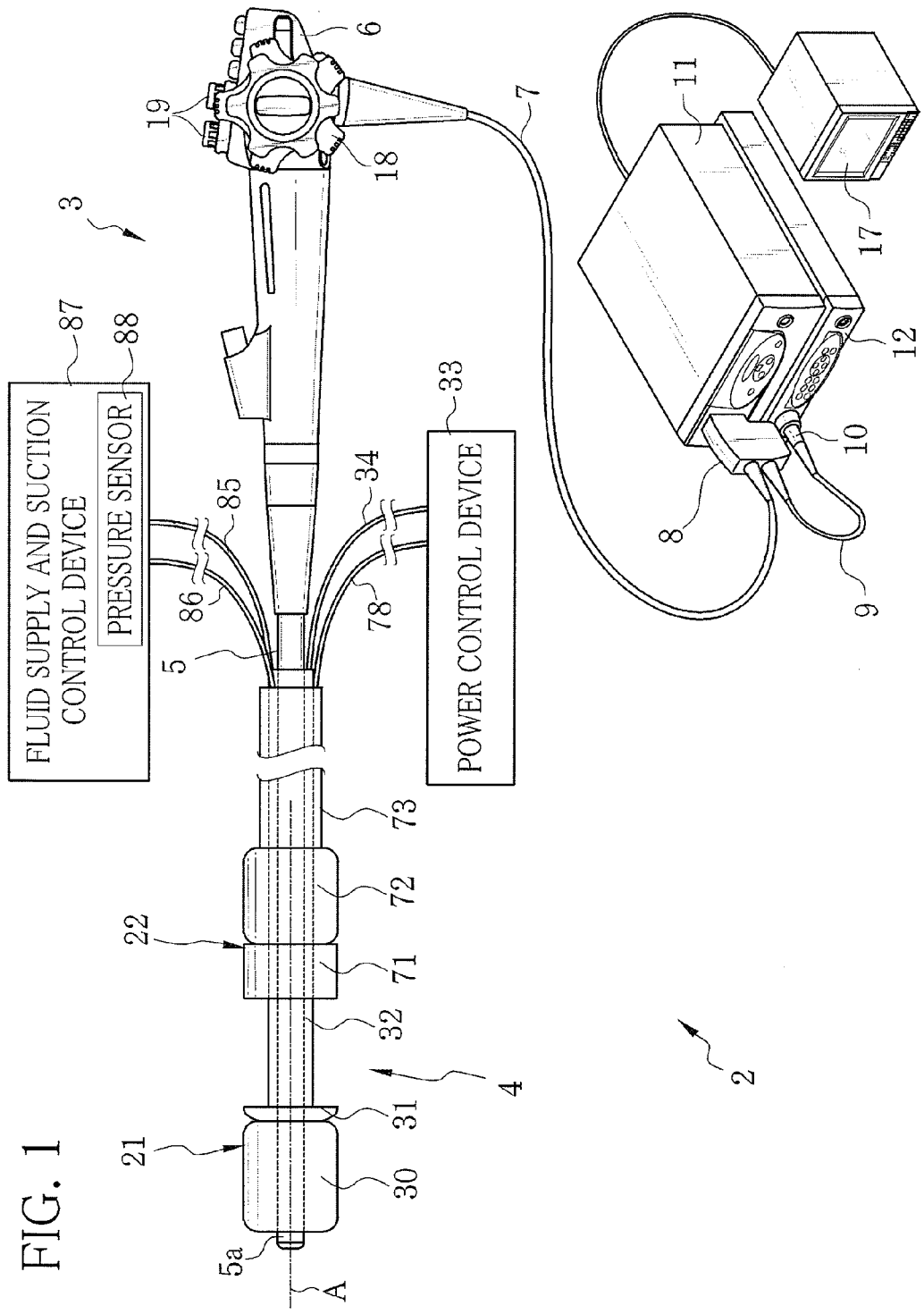
FIG. 1 is a schematic view of an endoscope system.

In FIG. 1, an endoscope system 2 is provided with an endoscope 3 and an anastomotic instrument 4. The endoscope 3 is constituted of an insert section 5 to be introduced into the alimentary canal such as colon, a handling section 6 coupled to the insert section 5 for holding the endoscope 3 and handling the insert section 5, and a universal cord 7 connected to the handling section 6. At an end of the universal cord 7, a light source connector 8 is provided. A cable 9 is branched out from the light source connector 8. At an end of the cable 9, a processor connector 10 is provided. The light source connector 8 is detachably connected to a light source device 11, and the processor connector 10 is detachably connected to a processor device 12, respectively.

Figure 2:
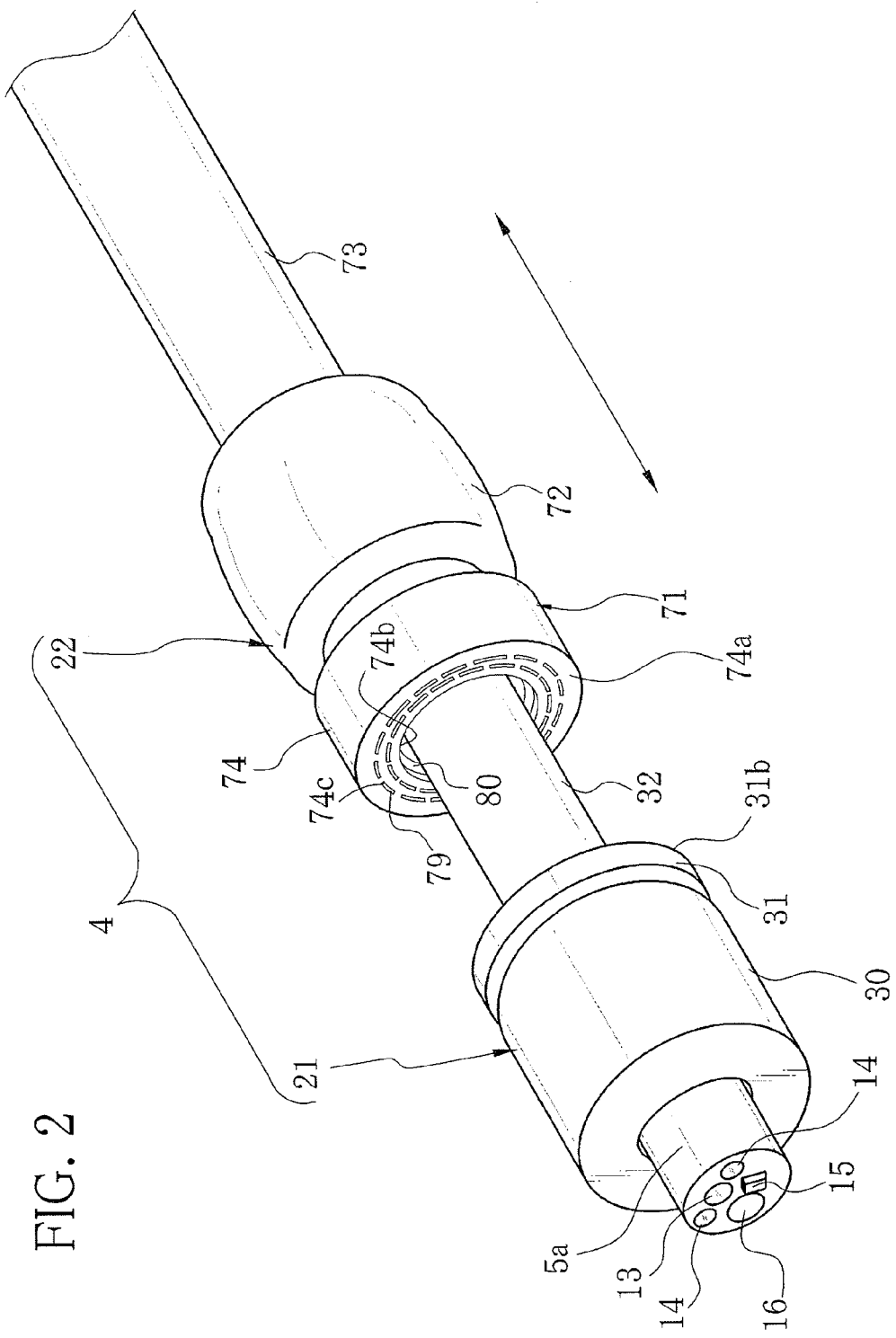
FIG. 2 is a perpendicular view of an appearance of an anastomotic instrument.

The insert section 5 is a flexible tube. As shown in FIG. 2, at a distal end portion 5a of the insert section 5, there are provided an image capturing window 13, lighting windows 14, an air/water feeding nozzle 15, and a forceps channel outlet 16, and the like. The two lighting windows 14 are disposed symmetrically with respect to the image capturing window 13.

Behind the image capturing window 13, there are provided an objective optical system for taking in an image of an internal body part to be imaged, and a solid-state imaging device such as a CCD or CMOS image sensor to capture the image of the internal body part. The solid-state imaging device is connected to the processor device 12 by a signal cable, which passes through the insert section 5, the handling section 6, and the universal cord 7 and reaches the processor connector 10. The image of the internal body part taken through the image capturing window 13 is formed on alight receiving surface of the solid-state imaging device, and converted into an image signal. The processor device 12 receives the image signal from the solid-state imaging device through the signal cable, and applies various types of image processing to the image signal. The image signal is converted into a video signal, and displayed as a live image on a monitor 17 (see FIG. 1), which is connected to the processor device 12 via a cable.

Light exit ends of a light guide are disposed behind the lighting windows 14, respectively. The light guide leads light emitted from the light source device 11. The light guide passes through the insert section 5, the handling section 6, and the universal cord 7, and reaches the light source connector 8. The light led by the light guide is applied to the internal body part to be imaged through the lighting windows 14.

The handling section 6 includes an angle knob 18, operation buttons 19, and the like. The angle knob 18 is rotated to adjust a direction of the insert section 5. The operation buttons 19 are used in various operations including air feeding, water feeding, air suction, and the like.

As shown in FIG. 2, the anastomotic instrument 4 is attached to the insert section 5 of the endoscope 3. The insert section with the anastomotic instrument 4 is inserted into the alimentary canal. The anastomotic instrument 4 is constituted of a first unit 21 and a second unit 22.

The first unit 21 includes a self-propellable apparatus 30 and an anvil 31 that are integrated with each other. The first unit 21 is attached to the side of a distal end of the insert section 5. A first sheath 32 is provided on the side of a proximal end of the self-propellable apparatus 30 and the anvil 31. The anvil 31 composes an anastomotic section together with a cartridge 71 of the second unit 22, as described later on. The anvil 31 has approximately the shape of a disk, and has an opening 31a (see FIG. 3) in the center thereof. The size of the opening 31a corresponds with the outside diameter of the first sheath 32. The first sheath 32 is fitted on the insert section 5, and the anvil 31 is fitted on an end portion of the first sheath 32.

The self-propellable apparatus 30, which is known by U.S. Patent Application Publication No. 2010/0198011 and the like, moves the insert section 5 forward or backward inside the alimentary canal. As shown in FIG. 1, the self-propellable apparatus 30 is driven by electric power supplied from a power control device 33. A cable 34 to supply the electric power to the self-propellable apparatus 30 is connected to the power control device 33.

The power control device 33 is connected to an operation unit (not shown). The operation unit is provided with buttons to issue forward-moving, backward-moving, and stopping commands to the self-propellable apparatus 30. The power control device 33 controls electric power supply in response to operation on the operation unit.

The cable 34 extends between the first sheath 32 and the insert section 5. Note that, the self-propellable apparatus 30 and the anvil 31 may be directly attached to the insert section 5 without provision of the first sheath 32. In this case, the cable 34 may be fixed on the insert section 5 with glue or the like along the entire insert section 5, or the insert section 5 may have a cable channel through which the cable 34 extends.

Figure 3:
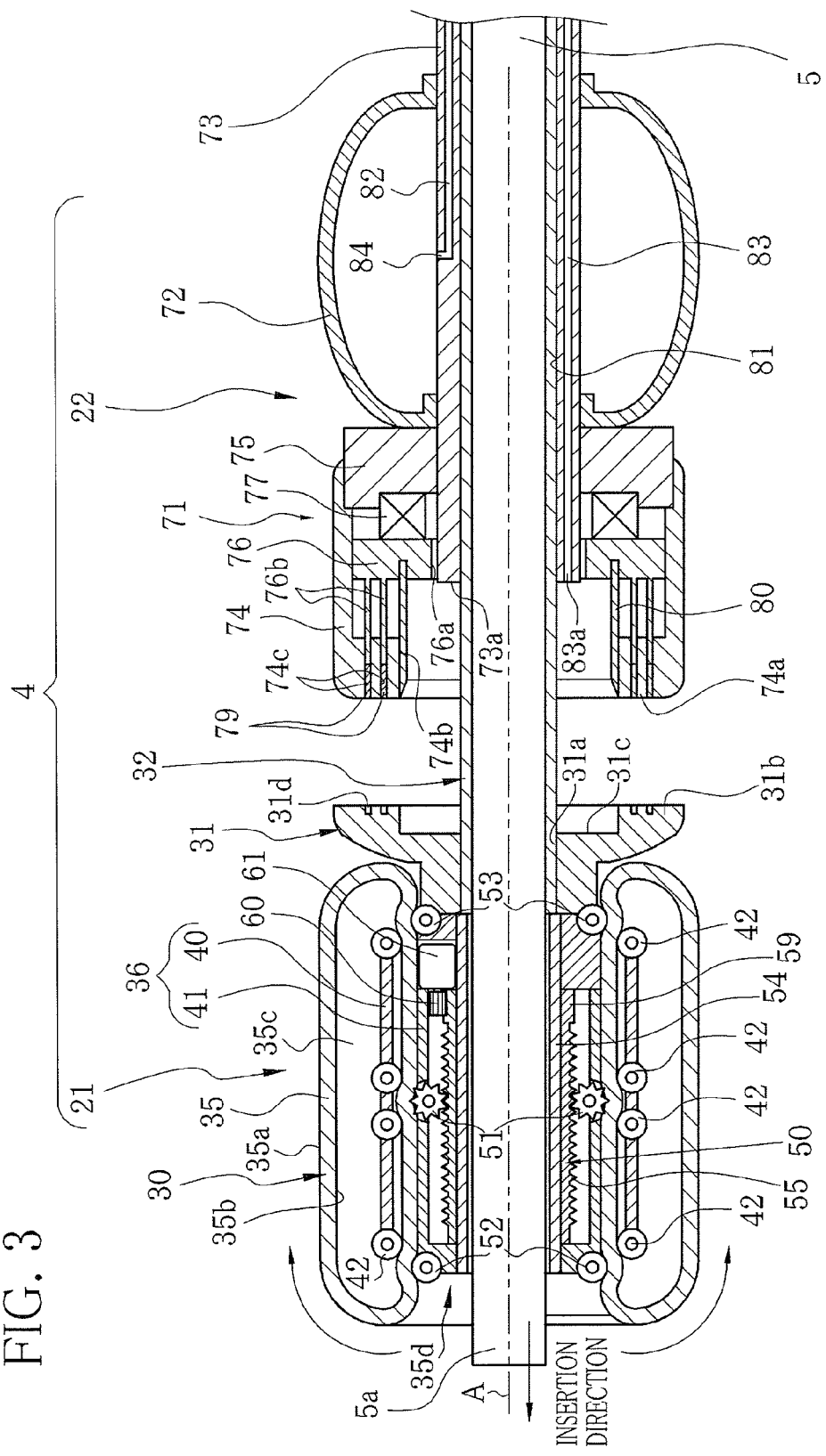
FIG. 3 is a cross sectional view of essential parts of the anastomotic instrument.

As shown in FIG. 3, the self-propellable apparatus 30 has a bladder 35. The bladder 35 makes contact with an interior wall of the alimentary canal, and produces a propelling force to move the self-propellable apparatus 30 forward to an insertion direction of the insert section 5 of the endoscope 3. The bladder 35 has the shape of a toroid (doughnut) centered on a line A, and has a single exterior surface 35a and a single interior surface 35b. The bladder 35 is made of a flexible material. To be more specific, the bladder 35 is preferably made of biocompatible plastic such as polyvinyl chloride, a polyamide resin, fluoroplastic, or the like.

An interior volume 35c of the bladder 35, which is defined by the interior surface 35b of the bladder 35, contains or is filled with fluid, gas, liquid, or combination thereof to keep a toroidal shape. Thus, the exterior surface 35a of the bladder 35 makes contact with the interior wall of the alimentary canal.

To move the self-propellable apparatus 30 forward in the insertion direction, the exterior surface 35a of the bladder 35 moves in the direction opposite to the insertion direction, while maintaining contact with the interior wall of the alimentary canal. Then, the exterior surface 35a makes a 180° turn at a rear end, and is folded back inwardly. Thereafter, the exterior surface 35a moves in the insertion direction at a medial side of the bladder 35, and makes a 180° turn again at a front end so as to be folded back outwardly. By circulation of the bladder 35 in the direction opposite to the insertion direction on an outer side and in the insertion direction on the medial side, as described above, the insert section 5 of the endoscope 3 moves forward. To move the self-propellable apparatus 30 backward in the direction opposite to the insertion direction, on the other hand, the exterior surface 35a of the bladder 35 is circulated in a direction opposite to above.

The bladder 35 is supported by a frame 36. The frame 36 includes a first support structure 40 and a second support structure 41. The first support structure 40 having the shape of a cylinder is disposed inside the interior volume 35c of the bladder 35. The second support structure 41 is disposed in a central cavity 35d around the center line A of the toroid. To the first support structure 40, a plurality of driven rollers 42 are rotatably attached along the center line A at predetermined angular intervals in a circumferential direction.

The second support structure 41 contains a worm gear 50. Also, the second support structure 41 rotatably supports transmission gears (pinion gears) 51 and stabilizing rollers 52 and 53, and has the anvil 31 fixed on the side of the proximal end. On the second support structure 41, a cylindrical attachment 54 is fixed. The cylindrical attachment 54 is fitted on the distal end portion 5a of the insert section 5, while rotatably supporting the worm gear 50.

The worm gear 50 has the shape of a cylinder that is rotationally symmetric with respect to the center line A. The worm gear 50 is fitted onto the attachment 54. The worm gear 50 is a driving section of the bladder 35. A helical thread 55 is formed about the center line A in an outside surface of the worm gear 50.

The transmission gears 51 engage with the thread 55 of the worm gear 50. Each transmission gear 51 partly protrudes from an opening formed in the second support structure 41 to come into contact with the exterior surface 35a of the bladder 35. The plural driven rollers 42 make contact with the bladder 35, and catch and hold the bladder 35 with the transmission gears 51 and the stabilizing rollers 52 and 53.

At a rear end of the worm gear 50, there is formed a gear train 59 having teeth arranged in a circumferential direction. A pinion 60 is engaged with the gear train 59. The pinion 60 is coaxial with a rotation axis of a pulse motor 61, being a drive motor. The pulse motor 61 is fixed to the second support structure 41. The cable 34 described above is connected to the pulse motor 61 through a not-shown hole formed in the attachment 54. Upon supplying electric power (drive pulse) from the power control device 33 to the pulse motor 61 through the cable 34, the pulse motor 61 drives the pinion 60. Rotation of the pinion 60 drives the gear train 59, and rotates the worm gear 50.

The worm gear 50 driven by the pinion 60 rotates about the center line A, and drives the bladder 35 via the transmission gears 51. The bladder 35 moves (circulates) in the insertion direction or the direction opposite to the insertion direction, in accordance with a rotation direction of the worm gear 50 (namely, in accordance with a rotation direction of the pulse motor 61).

The second unit 22 is disposed on the side of a proximal end of the insert section 5 relative to the first unit 21. The second unit 22 is constituted of the cartridge 71, a balloon 72, and a second sheath 73. The cartridge 71 includes a cylindrical holder 74, a base 75, a pusher 76, and an actuator 77. The holder 74 faces the anvil 31 of the first unit 21. The base 75 is fixed to the holder 74 on the side of a proximal end. The pusher 76 is disposed in internal space of the holder 74 and the base 75.

In the holder 74, an opening 74b is formed in the center of a surface 74a opposed to the anvil 31 to pass a cutter 80 therethrough. Plural staple chambers 74c, each of which contains a U-shaped staple 79, are concentrically formed around the opening 74b. The staple chambers 74c are arranged in two concentric circles. Each staple chamber 74c is open to the opposed surface 74a of the holder 74, and is communicated with the internal space of the holder 74 on the side of the proximal end.

The pusher 76 has approximately the shape of a disk. A gap 76a is formed in the center of the pusher 76 to pass the second sheath 73 therethrough. To the pusher 76, the cylindrical cutter 80 is fixed concentrically with the pusher 76. The pusher 76 has a lot of staple pusher pieces 76b formed around the cutter 80. The staple pusher pieces 76b are arranged in two concentric circles, so as to correspond to the staple chambers 74c. The staple pusher pieces 76b of the pusher 76 hold the staples 79, which are inserted into the staple chambers 74c from the side of the proximal end and contained therein, and push the staples 79 upon operation of a stapler.

The base 75 is fitted on an end of the second sheath 73. The actuator 77 is disposed between the pusher 76 and the base 75. The actuator 77 is a solenoid, for example. The actuator 77 is connected to the power control device 33 through a cable 78 (see FIG. 1). The cable 78 extends between the first sheath 32 and the second sheath 73, for example. When the actuator 77 is driven by control of the power control device 33, the actuator 77 thrusts the pusher 76 to the side of the distal end. Upon a thrust of the pusher 76 by the actuator 77, the cutter 80 protrudes from the opposed surface 74a to the anvil 31. Also, the staples 79 contained in the staple chambers 74c are pushed by the staple pusher pieces 76b, and protrude from the opposed surface 74a to the anvil 31. In the anvil 31, a concave section 31c to receive the cutter 80 and staple forming grooves 31d disposed around the concave section 31c are formed in a surface 31b opposed to the cartridge 71.

In the anastomotic section consisting of the anvil 31 and the cartridge 71, when the opposed surfaces 31b and 74a catch living body tissue composing the interior wall of the alimentary canal, the pusher 76 is thrust to the side of the distal end by drive of the actuator 77, so as to protrude the cutter 80 and the staples 79 from the opposed surface 74a. Therefore, the cutter 80 that has protruded to the concave section 31c of the anvil 31 resects the living body tissue. Also, the staples 79 are struck into circumferential edges of the resected alimentary canal, and ends of the staples 79 are folded by the staple forming grooves 31d to join the circumferential edges of the alimentary canal again.

The second sheath 73 is disposed, such that its end surface 73a is exposed from the gap 76a of the pusher 76 and faces the opposed surface 31b of the anvil 31. In the second sheath 73, a first sheath insertion conduit 81, a fluid supply/suction channel 82 for the balloon 72, and an air suction channel 83 are formed along an axial direction of the second sheath 73. The first sheath 32 is inserted through the first sheath insertion conduit 81, and the first sheath insertion conduit 81 is preferably coated with a lubricating coating material or the like to improve lubrication.

The balloon 72 has approximately the shape of a cylinder the middle of which puffs up. Both distal and proximal ends of the balloon 72 are fixed on an outer periphery of the second sheath 73 by winding of a thread, glue, or the like. A distal end of the fluid supply/suction channel 82 is closed in the vicinity of the distal end of the balloon 72. The fluid supply/suction channel 82 communicates with an outlet 84, which is formed in the outer periphery of the second sheath 73. The outlet 84 is formed in a position corresponding to an attachment position of the balloon 72. Since fluid is supplied to or sucked out from the balloon 72 through the outlet 84, the balloon 72 is expanded or shrunk. A proximal end of the fluid supply/suction channel 82 is connected to a tube 85 (see FIG. 1).

A suction port 83a of the air suction channel 83 on the side of the distal end communicates with the end surface 73a of the second sheath 73, and faces the opposed surface 31b of the anvil 31 through the opening 74b and the gap 76a. A proximal end of the air suction channel 83 is connected to a tube 86 (see FIG. 1).

The fluid supply/suction channel 82 and the air suction channel 83 are connected to a fluid supply and suction control device 87 (see FIG. 1) through the tubes 85 and 86, respectively. The fluid supply and suction control device 87 has the function of supplying or sucking out fluid such as air, and is connected to a not-shown operation unit. The fluid supply and suction control device 87 sucks out the fluid through the air suction channel 83 and the tube 86 in response to operation on the operation unit, so as to bring space enclosed by the first and second units 21 and 22 into negative pressure. The fluid supply and suction control device 87 also supplies air for expansion to the balloon 72 through the fluid supply/suction channel 82 and the tube 85, and keeps air pressure at a constant level to maintain an expanded state of the balloon 72.

Note that, the fluid supply and suction control device 87 includes a pressure sensor 88 as a pressure gage. The pressure sensor 88 detects a suction pressure level at which the fluid supply and suction control device 87 sucks out air from the space enclosed by the first and second units 21 and 22. The fluid supply and suction control device 87 displays the suction pressure level detected by the pressure sensor 88 on a not-shown monitor. When the suction pressure level displayed on the monitor is a predetermined value or more, the space enclose by the first and second units 21 and 22 is judged to be the negative pressure.

As described above, the cartridge 71 and the balloon 72 are fixed on the second sheath 73, and the second sheath 73 is slidable relative to the first sheath 32 along an axial direction. Thus, the second unit 22 is slidable between a "catch position" in which the second unit 22 approaches the first unit 21 to catch the living body tissue composing the interior wall of the alimentary canal between the opposed surfaces 31b and 74a, and a "retracted position" in which the second unit 22 is away from the first unit 21.

Next, operation of the endoscope system 2 having above structure will be described with referring to FIGS. 4A to 5C. First, the anastomotic instrument 4 is attached to the insert section 5 of the endoscope 3. In this attachment process, the first sheath 32 is fitted on the insert section 5, and the second sheath 73 having the cartridge 71 and the balloon 72 is fitted on the first sheath 32. Then, the self-propellable apparatus 30 and the anvil 31 are attached to a distal end portion of the first sheath 32. After turning on the light source device 11, the processor device 12, the power control device 33, the fluid supply and suction control device 87, the operation unit and the like, which are described above, to make preparations for a surgical operation, the distal end portion 5a of the insert section 5 of the endoscope 3 is inserted into the alimentary canal of a patient.

After the distal end portion 5a reaches a predetermined position in the alimentary canal, for example, just before the sigmoid, the operation unit of the power control device 33 is operated to start supplying the electric power (drive pulse) to the self-propellable apparatus 30. Upon input of the forward-moving command, the drive pulse is supplied to rotate the pulse motor 61 forward, and the pinion 60 is rotated in a predetermined direction. In response to the rotation of the pinion 60, the worm gear 50 is rotated, and the bladder 35 is circulated in a direction shown by an arrow of FIG. 3. The bladder 35 is in contact with the interior wall of the alimentary canal, and produces the propelling force to move the distal end portion 5a forward in the insertion direction. The self-propellable apparatus 30 hauls the interior wall of the alimentary canal front to back owing to the propelling force, and accordingly moves the distal end portion 5a of the endoscope 3 forward along the interior wall of the alimentary canal.

Upon input of the backward-moving command, the power control device 33 supplies the drive pulse to the pulse motor 61 to rotate the pinion 60 in a backward direction. As a result, the self-propellable apparatus 30 moves backward. Furthermore, upon input of the stopping command by operation of a button of the operation unit, the power control device 33 stops supplying the drive pulse, to stop the self-propellable apparatus 30. Appropriately performing above operations allows the distal end portion 5a to reach the depths of the alimentary canal.

At this time, balloon 72 may be appropriately expanded by operation on the operation unit of the fluid supply and suction control device 87. While the second sheath 73 is fixed in the alimentary canal, the self-propellable apparatus 30 may move forward to propel the distal end portion 5a and the first unit 21. Then, after the balloon 72 is shrunk, the second sheath 73 may be manually pushed to slide the second sheath 73 relative to the first sheath 32, so that the second unit 22 is advanced into the depths of the alimentary canal.

Figure 4A:
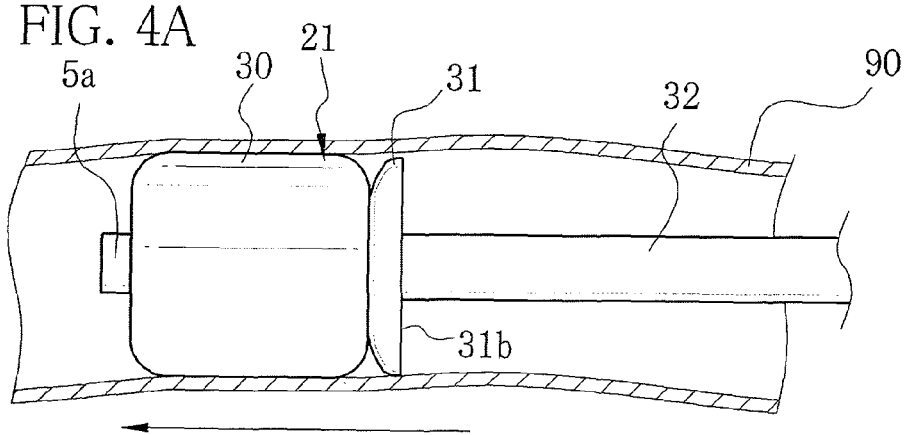
FIGS. 4A to 4C are explanatory views of a surgical process in which the anastomotic instrument is inserted into the depths of the alimentary canal, and space enclosed by first and second units is brought into negative pressure.
Figure 4B:
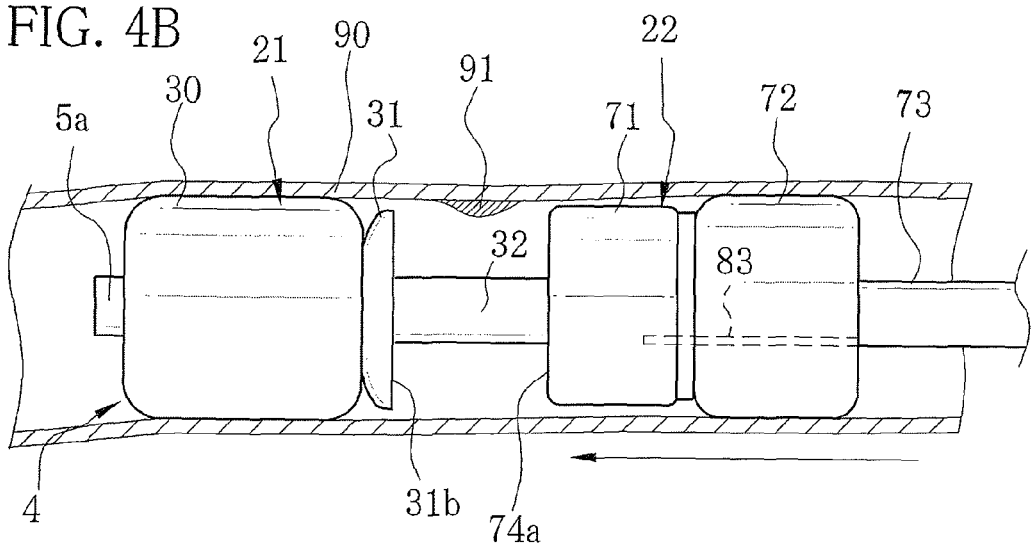

Thereafter, as shown in FIG. 4A, when the distal end portion 5a reaches the depths of the alimentary canal 90, the position of the living body tissue to be resected is checked based on the live image displayed on the monitor 17. Then, the second unit 22 is moved forward by manually pushing the second sheath 73, as described above. In this manner, the self-propellable apparatus 30 moves forward or backward and is stopped, such that the living body tissue 91 checked on the monitor 17 is situated between the first and second units 21 and 22, as shown in FIG. 4B. At this time, the second unit 22 is brought into the retracted position, leaving a predetermined distance away from the first unit 21.

After the first and second units 21 and 22 are situated across living body tissue 91 of the alimentary canal 90, the balloon 72 is expanded to predetermined volume in response to operation on the operation unit of the fluid supply and suction control device 87, such that the second unit 22 comes into contact with the interior wall of the alimentary canal 90. At this time, the first unit 21 is in contact with the interior wall of the alimentary canal 90 due to the fluid contained in the bladder 35, as described above. Therefore, the space that is enclosed by the first and second units 21 and 22 inside the alimentary canal 90 and contains the living body tissue is tightly sealed.

Figure 4C:
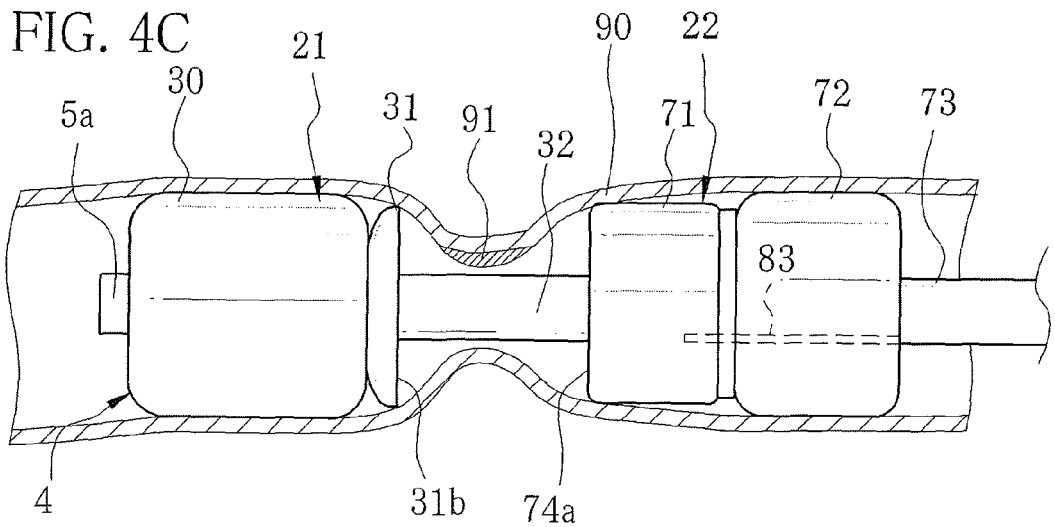

Then, as shown in FIG. 4C, while the space between the first and second units 21 and 22 inside the alimentary canal 90 is sealed tightly, the operation unit of the fluid supply and suction control device 87 is operated to bring the sealed space into the negative pressure. Thus, the space between the first and second units 21 and 22 is brought into the negative pressure, and the internal diameter of the alimentary canal 90 is shrunk in the space containing the living body tissue 90. Thereby, the interior wall of the alimentary canal 90 is caught between the opposed surfaces 31b and 74a, so as to be resected by the cutter 80 and stapled by the staples 79. Note that, at this time, the suction pressure level displayed on the monitor of the fluid supply and suction control device 87 facilitates recognition that the space enclosed by the first and second units 21 and 22 has been brought into the negative pressure.

Figure 5A:
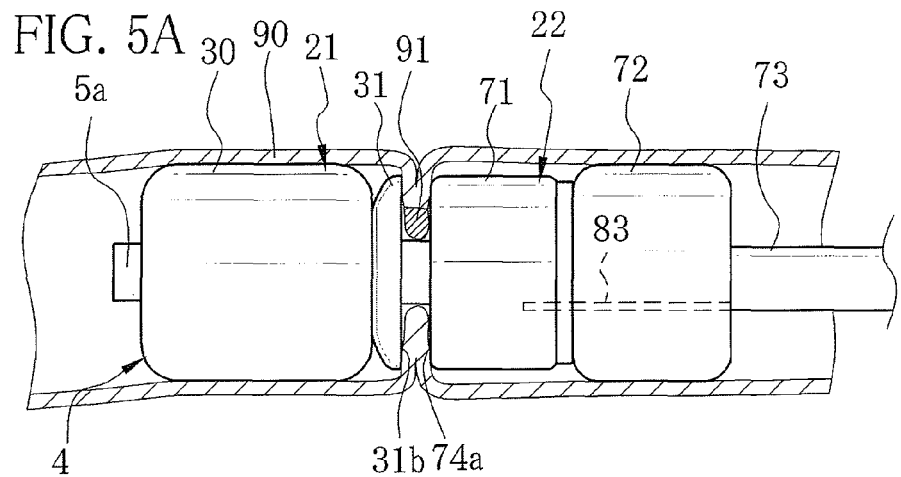
FIGS. 5A to 5C are explanatory views of the surgical process in which living body tissue situated in the depths of the alimentary canal is resected, while the space enclosed by the first and second units is brought into the negative pressure.
Figure 5B:
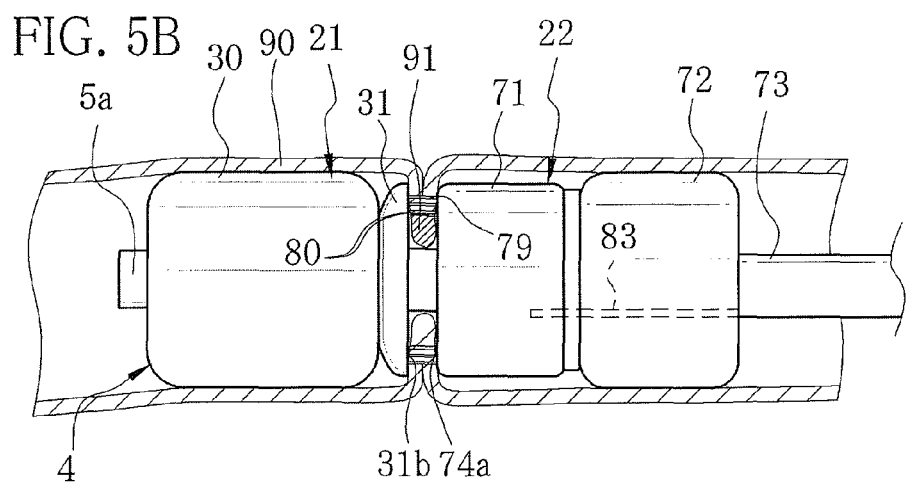

Then, as shown in FIG. 5A, while the space enclosed by the first and second units 21 and 22 is kept at the negative pressure, the insert section 5 is fixed, and the second sheath 73 is manually pushed into the insertion direction to shift the second unit 22 from the retracted position to the catch position. While the opposed surfaces 31b and 74a keep catching the interior wall of the alimentary canal 90 containing the living body tissue 91, the operation unit of the power control device 33 is operated to drive the actuator 77. Therefore, as shown in FIG. 5B, the cutter 80 and the staples 79 protrude from the opposed surface 74a. Thus, the living body tissue 91 is resected from the interior wall of the alimentary canal 90, and the staples 79 are struck into circumferential edges of an incision of the interior wall to join the alimentary canal 90 again.

Figure 5C:
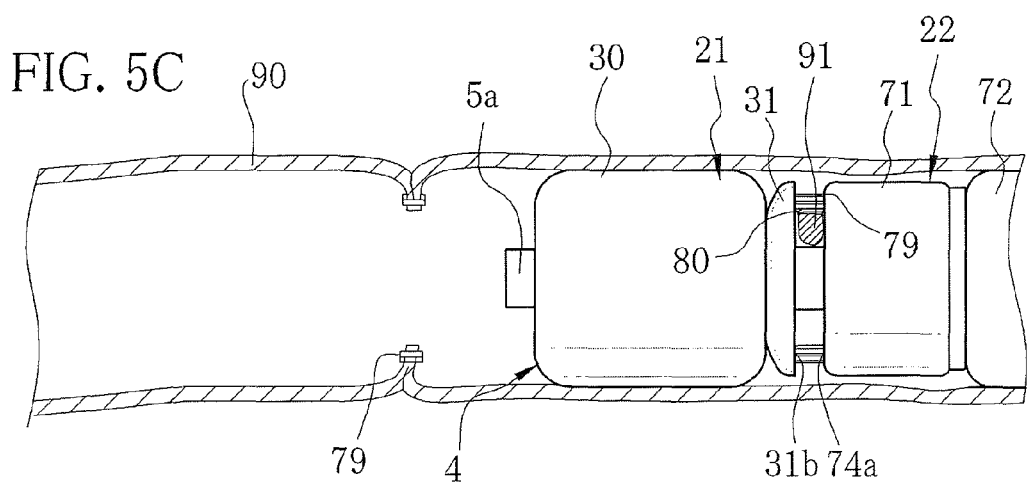

After that, as shown in FIG. 5C, the insert section 5 having the anastomotic instrument 4 is pulled out of the alimentary canal 90. At this time, the resected living body tissue 91 is brought out from the alimentary canal 90, while being caught between the anvil 31 and the cartridge 71. As described above, the anastomotic instrument 4 allows certain resection of the living body tissue 91 situated in the depths of the alimentary canal.

In the above embodiment, the cartridge 71 that protrudes the cutter 80 and strikes the stables 79 around the cutter 80 is provided in the second unit 22, while the anvil 31 that receives the cutter 80 and the staples 79 is provided in the first unit 21. However, the cartridge may be provided in the first unit 21, while the anvil may be provided in the second unit 22, instead.

In the above embodiment, the first unit 21 is provided with the self-propellable apparatus 30, while the second unit 22 is provided with the balloon 72. However, the first unit 21 may be provided with the balloon, while the second unit 22 may be provided with the self-propellable apparatus. Besides, both the first and second units 21 and 22 may have each of the self-propellable apparatus and the balloon. If the second unit 22 is provided with the self-propellable apparatus, the second unit 22 is shifted to the catch position by the propelling force of the self-propellable apparatus. If both the first and second units 21 and 22 have the balloon, the two balloons are alternately expanded and fixed in the alimentary canal, and the insert section 5 and the second sheath 73 are pushed alternately to insert the first and second units 21 and 22 to the depths of the alimentary canal.

In the above embodiment, the suction port of the suction device is provided in the second unit 22, but may be provided in the first unit 21 instead. In this case, the suction port is preferably disposed so as to face an opposed surface of the second unit 22.

In the above embodiment, the pressure sensor 88 integrated in the fluid supply and suction control device 87 is used as the pressure gage for detecting the suction pressure level, but any device is usable as long as it can detect the suction pressure level in sucking out air from the space enclosed by the first and second units 21 and 22. For example, a pressure sensor provided separately from the fluid supply and suction control device 87 may be provided in one of the first and second units 21 and 22. Plural pressure sensors for detecting the suction pressure level in the space enclosed by the first and second units 21 and 22 may be provided along a circumferential direction at constant angular intervals. In this case, when all of the pressure sensors disposed at the constant angular intervals indicate a predetermined value or more, it is possible to recognize that the air is sucked out evenly in the circumferential direction throughout the space enclosed by the first and second units 21 and 22, and more precisely bring the space enclosed by the first and second units 21 and 22 into the negative pressure.

In the above embodiment, the second sheath 73 is manually moved forward to catch the alimentary canal 90 between the first and second units 21 and 22. Instead of this, the first unit 21 may be moved backward by reverse rotation of the pulse motor 61, and catches the alimentary canal 90 with the second unit 22.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. An anastomotic instrument comprising:
a first unit attached to an insert section of an endoscope to be inserted into an alimentary canal on a side of a distal end of said insert section;
a second unit set on said insert section on a side of a proximal end of said insert section relative to said first unit;
a suction device for sucking out fluid from space enclosed by said first and second units in said alimentary canal so as to bring said space into negative pressure, and shrinking said alimentary canal in said space;
a resecting device for shifting one of said first and second units relative to the other one of said first and second units, and resecting living body tissue of said alimentary canal in a state of being caught between said first and second units; and
a fastening device for joining said alimentary canal so as to close an incision of said living body tissue,
wherein said first unit has a first through hole that penetrates from a proximal end to a distal end of said first unit and has an inner diameter substantially equal to an outer diameter of said insert section, and
wherein said second unit has a second through hole that penetrates from a proximal end to a distal end of said second unit and has an inner diameter substantially equal to said outer diameter of said insert section.

2. The anastomotic instrument according to claim 1, wherein said resecting device includes a cylindrical cutter, and said cutter protrudes from an opposed surface across which said first and second units are opposed, and cuts said living body tissue.

3. The anastomotic instrument according to claim 2, wherein said fastening device includes a staple struck around said cutter by a stapler to join edges of said incision of said alimentary canal resected by said cutter.

4. The anastomotic instrument according to claim 1, wherein a first sheath is coupled to said first through hole of said first unit, and a second sheath is coupled to said second through hole of said second unit, and said first and second sheaths are fitted on said insert section, and
wherein said second sheath has a diameter larger than that of said first sheath and is fitted onto an outer peripheral surface of said first sheath.

5. An anastomotic instrument comprising:
a first unit attached to an insert section of an endoscope to be inserted into an alimentary canal on a side of a distal end of said insert section;
a second unit set on said insert section on a side of a proximal end of said insert section relative to said first unit;
a suction device for sucking out fluid from space enclosed by said first and second units in said alimentary canal so as to bring said space into negative pressure, and shrinking said alimentary canal in said space;

a resecting device for shifting one of said first and second units relative to the other one of said first and second units, and resecting living body tissue of said alimentary canal in a state of being caught between said first and second units; and a fastening device for joining said alimentary canal so as to close an incision of said living body tissue, wherein at least one of said first and second units has a self-propellable apparatus for propelling said insert section into depths of said alimentary canal.

6. An anastomotic instrument comprising:

a first unit attached to an insert section of an endoscope to be inserted into an alimentary canal on a side of a distal end of said insert section;

a second unit set on said insert section on a side of a proximal end of said insert section relative to said first unit;

a suction device for sucking out fluid from space enclosed by said first and second units in said alimentary canal so as to bring said space into negative pressure, and shrinking said alimentary canal in said space;

a resecting device for shifting one of said first and second units relative to the other one of said first and second units, and resecting living body tissue of said alimentary canal in a state of being caught between said first and second units; and a fastening device for joining said alimentary canal so as to close an incision of said living body tissue, wherein at least one of said first and second units has a balloon to be expanded with air sent inside.

7. The anastomotic instrument according to claim 6, wherein while said suction device is reducing pressure of said space enclosed by said first and second units, said first and second units tightly seal said space by a self-propelling apparatus or said balloon making contact with said alimentary canal.

8. An anastomotic instrument comprising:

a first unit attached to an insert section of an endoscope to be inserted into an alimentary canal on a side of a distal end of said insert section;

a second unit set on said insert section on a side of a proximal end of said insert section relative to said first unit;

a suction device for sucking out fluid from space enclosed by said first and second units in said alimentary canal so as to bring said space into negative pressure, and shrinking said alimentary canal in said space;

a resecting device for shifting one of said first and second units relative to the other one of said first and second units, and resecting living body tissue of said alimentary canal in a state of being caught between said first and second units; and a fastening device for joining said alimentary canal so as to close an incision of said living body tissue, further comprising:

a pressure gage for detecting said pressure of said space enclosed by said first and second units, while said suction device is sucking out said fluid from said space.

9. An endoscope system comprising:

(A) an endoscope including:

an insert section to be introduced into an alimentary canal; and a handling section coupled to said insert section and used in operation of said endoscope;

(B) an anastomotic instrument including:

a first unit attached to said insert section on a side of a distal end of said insert section;

a second unit set on said insert section on a side of a proximal end of said insert section relative to said first unit;

a suction device for sucking out fluid from space enclosed by said first and second units in said alimentary canal so as to bring said space into negative pressure, and shrinking said alimentary canal in said space;

a resecting device for shifting one of said first and second units relative to the other one of said first and second units, and resecting living body tissue of said alimentary canal in a state of being caught between said first and second units; and a fastening device for joining said alimentary canal so as to close an incision of said living body tissue, wherein said first unit has a first through hole that penetrates from a proximal end to a distal end of said first unit and has an inner diameter substantially equal to an outer diameter of said insert section, and wherein said second unit has a second through hole that penetrates from a proximal end to a distal end of said second unit and has an inner diameter substantially equal to said outer diameter of said insert section.

\* \* \* \* \*